US010794852B2

(12) United States Patent
Rubin et al.

(10) Patent No.: US 10,794,852 B2
(45) Date of Patent: Oct. 6, 2020

(54) ELECTROCHEMICAL QUANTITATION OF AUTOANTIBODIES

(71) Applicants: STC.UNM, Albuquerque, NM (US); Robert L. Rubin, Tijeras, NM (US); Konstantin N. Konstantinov, Albuquerque, NM (US); David A. Wall, Albuquerque, NM (US)

(72) Inventors: Robert L. Rubin, Tijeras, NM (US); Konstantin N. Konstantinov, Albuquerque, NM (US); David A. Wall, Albuquerque, NM (US)

( * ) Notice: Subject to any disclaimer, the term of this patent is extended or adjusted under 35 U.S.C. 154(b) by 148 days.

(21) Appl. No.: 15/115,033

(22) PCT Filed: Jan. 29, 2015

(86) PCT No.: PCT/US2015/013434
§ 371 (c)(1),
(2) Date: Jul. 28, 2016

(87) PCT Pub. No.: WO2015/116769
PCT Pub. Date: Aug. 6, 2015

(65) Prior Publication Data
US 2016/0341687 A1 Nov. 24, 2016

Related U.S. Application Data

(60) Provisional application No. 61/932,840, filed on Jan. 29, 2014.

(51) Int. Cl.
*G01N 27/327* (2006.01)
*G01N 33/543* (2006.01)
(52) U.S. Cl.
CPC ..... *G01N 27/3273* (2013.01); *G01N 27/3276* (2013.01); *G01N 33/5438* (2013.01)

(58) Field of Classification Search
None
See application file for complete search history.

(56) References Cited

U.S. PATENT DOCUMENTS

2009/0242429 A1  10/2009  Sitdikov et al.
2009/0288960 A1* 11/2009  Rubin ............... G01N 33/5438
                                                   205/777.5

OTHER PUBLICATIONS

"Electrochemical Quantitation of Antinuclear Antibodies (ANA) in Patients at the Point-of-Care" Manuscript, Submitted to the 9th International Congress on Autoimmunity conference in Nice, France, on Mar. 26, 2014; 5 pages.

(Continued)

*Primary Examiner* — Eli S Mekhlin

(57) ABSTRACT

This disclosure describes, in one aspect, a device for electrochemical quantitation of autoantibodies. Generally, the device includes a housing that defines a plurality of channels and at least two reaction zones. A first reaction zone includes a porous membrane and a first electrode assembly in fluid communication with a first channel. The first reaction zone also includes a first plurality of autoantigens immobilized to the porous membrane. The first electrode assembly is in communication with an amperometric reader. A second reaction zone includes a porous membrane and a second electrode assembly in fluid communication with a second channel. The second reaction zone includes a second plurality of autoantigens immobilized to the porous membrane. The second electrode assembly is in communication with the amperometric reader. Finally, the device includes a source of negative pressure in fluid communication with the first reaction zone and the second reaction zone.

5 Claims, 9 Drawing Sheets

(56) References Cited

OTHER PUBLICATIONS

Burlingame et al., "Subnucleosome structures as substrates in enzyme-linked immunosorbent assays" Dec. 1990 *Immunol Methods*, vol. (134): pp. 187-199.

Konstantinov et al., "Rapid detection of anti-chromatin autoantibodies in human serum using a portable electrochemical biosensor" 2009 *Biosensors and Bioelectronics*, vol. (24): pp. 1949-1954.

Laemmli, "Cleavage of Structural Proteins during the Assembly of the Head of Bacteriophage T4" Aug. 1970 *Nature*, vol. (227): pp. 680-685.

Towbin et al., "Electrophoretic transfer of proteins from polyacrylamide gels to nitrocellulose sheets: procedure and some applications" 1979 *Proceedings of the National Academy of Sciences of the United States of America*, vol. (76): pp. 4350-4354.

PCT Patent Application No. PCT/US2015/013434, filed Jan. 29, 2015; International Search Report and Written Opinion dated May 11, 2015; 9 pages.

PCT Patent Application No. PCT/US2015/013434, filed Jan. 29, 2015; International Preliminary Report on Patentability dated Aug. 11, 2016; 8 pages.

\* cited by examiner

ELECTROCHEMICAL QUANTITATION OF AUTOANTIBODIES

CROSS-REFERENCE TO RELATED APPLICATION

This application is the §371 U.S. National Stage of International Application No. PCT/US2015/013434, filed 29 Jan. 2015, which claims priority to U.S. Provisional Patent Application Serial No. 61/932,840, filed Jan. 29, 2014, each of which is incorporated herein by reference.

SUMMARY

This disclosure describes, in one aspect, a device for electrochemical quantitation of autoantibodies. Generally, the device includes a housing that defines a plurality of channels and at least two reaction zones. A first reaction zone includes a porous membrane and a first electrode assembly in fluid communication with a first channel. The first reaction zone also includes a first plurality of autoantigens immobilized to the porous membrane. The first electrode assembly is in communication with an amperometric reader. A second reaction zone includes a porous membrane and a second electrode assembly in fluid communication with a second channel. The second reaction zone includes a second plurality of autoantigens immobilized to the porous membrane. The second electrode assembly is in communication with the amperometric reader. Finally, the device includes a source of negative pressure in fluid communication with the first reaction zone and the second reaction zone.

In some embodiments, the device can further include a third reaction zone that includes a porous membrane and a third electrode assembly in fluid communication with a third channel. The third reaction zone can include either a third plurality of autoantigens immobilized to the porous membrane or IgG immunoglobulin immobilized to the membrane. The third electrode assembly is in communication with the amperometric reader. The third reaction zone is in fluid communication with the source of negative pressure.

In another aspect, this disclosure describes a method of analyzing a biological sample for the presence of autoantibodies. Generally, the method includes providing any embodiment of the device summarized above, drawing at least a portion of a biological sample from a subject through the first reaction zone in fluid communication with the first channel, washing unbound components of the biological sample from the first reaction zone, drawing at least a portion of an anti-human IgG preparation through the first reaction zone in fluid communication with the first channel, the anti-human IgG comprising an enzyme that catalyzes an electrode-detectable reaction in the presence of a suitable substrate, washing unbound anti-human IgG from the first reaction zone, contacting the suitable substrate with the first reaction zone under conditions suitable for the enzyme to catalyze the electrode-detectable reaction, and measuring the electrode-detectable reaction. In some embodiments, the second and third reaction zone are subject only to the anti-human IgG enzyme conjugate and subsequent steps and serve as negative and positive controls, respectively, for each test.

In some embodiments, the method may be performed in no more than 30 minutes. Thus, in some embodiments, the method is suitable for use as a point-of-care diagnostic test.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
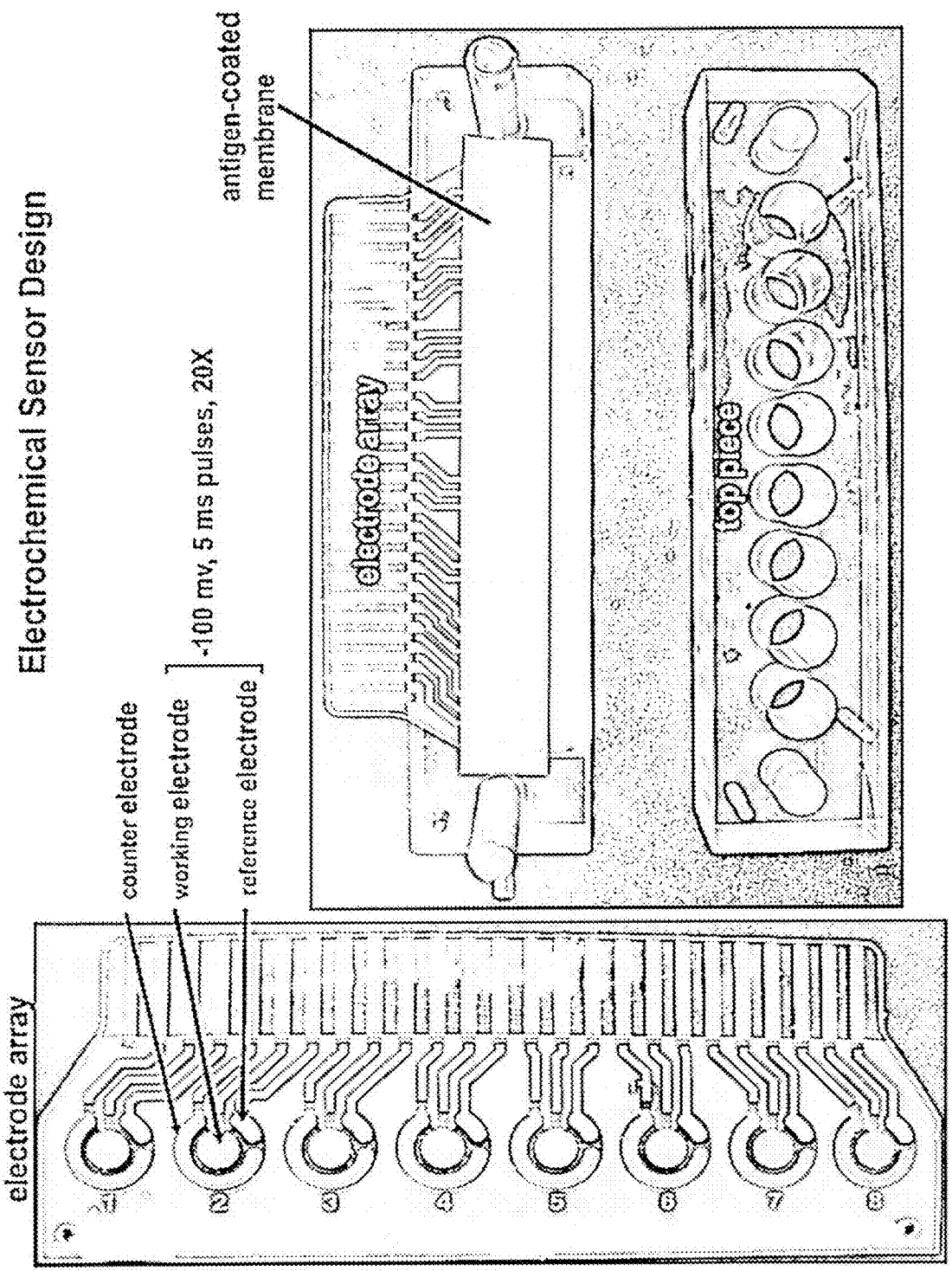
FIG. 1. An exemplary embodiment biosensor device.

Most autoimmune diseases are associated with autoantibodies, the detection of which can be useful to identify whether a patient has or is at risk of developing an autoimmune disease, define and/or classify disease, predict flares, and/or monitor the efficacy of therapy. Autoantibodies are markers of autoimmune disease across subspecialties such as, for example, neurology, infectious disease, oncology, and rheumatology. For example, the presence of total antinuclear antibodies (ANA)—of undefined specificity—often triggers follow-up diagnostic evaluation for diseases such as autoimmune liver diseases, drug-induced autoimmune syndromes, paraneoplastic diseases, systemic vasculitis, and a wide variety of rheumatological diseases. In many of these conditions, the presence of autoantibodies (e.g., ANA) constitutes part of the diagnostic criteria or classification criteria for those diseases. Therefore, testing for autoantibodies is tool at both the primary care and subspecialty settings indicating whether further clinical investigation may be necessary.

Conventional testing for autoantibodies is now performed exclusively in centralized clinical laboratories. This is a protracted, labor intensive, and expensive procedure that can slow the diagnostic process and restrict its use for a large segment of the population. The requirement for blood drawing, transport to the testing lab, blood processing, test execution, and communication of results creates a cumbersome, time consuming, error prone and expensive process which detracts from its diagnostic value.

An alternative to conventional testing for autoantibodies involves a test that may be completed while the patient remains in the clinic such as, for example, during the course of a routine clinic visit. This disclosure describes devices and methods that can provide a portable point-of-care (POC) test for autoantibodies that can be used in a primary care clinical setting, subspecialty care clinical setting, urgent care, or emergency room situation, with an emphasis on low cost, ease of use, and reliability. Successful development of a point-of-care autoantibody testing device can streamline detection of autoimmune-related diseases by shifting current practice from a centralized laboratory to a patient-centered environment, including remote or rudimentary clinical settings. (Konstantinov et al., 2013, *Autoimmunity Highlights* 4 (2), 55-61).

The devices and methods described herein involve biosensor technology that allows point-of-care analysis of a biological sample (e.g., a small blood, serum, or plasma sample) to determine whether the subject has or is at risk of having an autoimmune disease. In practice, the devices and methods may be used in the clinic by a health care professional so that the results can then be discussed with the subject during the visit. If results are positive and it is deemed appropriate by the health care professional, the patient can be immediately referred to a clinical specialist.

Real-time measurement of autoantibodies also can benefit practice in emergency and urgent care settings. Immediate serological information in these settings will provide considerable value for long-term patient care and an opportunity for an instant, result-deduced therapeutic action, avoiding delays and improving compliance especially in field-based and remote areas.

Devising a reliable assay for measuring a specific antibody in human serum is considerably more difficult that measuring most non-antibody analytes in biological fluids, because any one antibody specificity is usually a tiny fraction of all the antibody constituting total serum immunoglobulin. Non-specific binding of immunoglobulin may have impeded the development of a reliable antibody biosensor. This disclosure describes devices and methods that overcome this fundamental difficulty, allowing analysis of a fresh biological sample (e.g., blood, serum, or plasma) by an immunosensor that provides high accuracy and precision in quantification, large dynamic range, and adequate detection limit in testing for specific autoantibodies of importance in clinical practice.

In one aspect, this disclosure describes an electrochemical biosensor for quantitation of total ANA. The (total) ANA test is widely used as an initial screening test for any autoantibody specificity, in which technicians in centralized clinical laboratories measure the capacity of antibodies in patient's serum to bind cellular protein, nucleoprotein or nucleic acid within permeabilized cells using immunofluorescence microscopy. A positive ANA test suggests that the patient has or is developing an autoimmune disease, which requires further work-up to determine the precise autoantibody specificity. Prior to the current disclosure measuring total ANA by alternative immunoassays using a crude cellular extract was not feasible because solid supports usually employed do not have the capacity to immobilize the thousands of different cellular macromolecules with potential capacity to bind autoantibodies. Because the current device employs a membranous solid support with unusually high macromolecule binding capacity, a relatively large amount of a crude cellular extract supplemented with a chromatin solution can be immobilized. This permits the quantitation of total autoantibodies (e.g., total ANA) with sensitivity and specificity comparable to that of the conventional ANA test performed in a centralized clinical laboratory.

The devices described below can rapidly measure autoantibody of essentially any specificity in a fresh biological sample by virtue of the simple and flexible design of its fluidic and electronic components. Because the method for measuring total ANA employs as an autoantigen source a crude extract of animal tissue supplemented with chromatin, this test can be performed at relatively little cost. As used herein, the term "autoantigen" refers to a macromolecule derived from self-material (e.g., the subject's own tissue) that becomes the target of an antibody, manifested as an autoimmune disease. Autoantigens are not patient- or even species-specific, so that target antigens employed in autoantibody tests can be reliably derived from a wide variety of sources. In the current device, excess autoantigens are immobilized to a porous membrane. Using weak vacuum, a biological sample (e.g., blood, plasma, or serum) is slowly drawn through the membrane to which autoantigens have been immobilized at high density, promoting rapid binding of autoantibodies that are present in the patient sample. After washing to remove irrelevant immunoglobulin, an anti-human IgG conjugated to an enzyme that catalyzes an electrode-detectable reaction is rapidly drawn through the membrane by the same procedure. After another wash, an electrode assembly is inserted under the membrane, and a substrate of the enzyme is added. Real-time enzymatic activity is measured, which is proportional to the amount of autoantibody bound to autoantigen(s) immobilized on the membrane.

In some embodiments, described in more detail below, the device may be designed for simultaneously measuring autoantibodies in multiple patients. In other embodiments, also described in more detail below, a field-usable form of the device that is designed for measuring autoantibody (e.g., ANA) in an individual patient; this form of the device is designed to be portable for the purpose of quantifying ANA during the brief time a patient remains in the clinic, making it feasible to use as a point-of-care diagnostic aid.

ANA Detection Method

Conventional antibody assays typically employ a single purified target (or a selected array of purified targets) present in sufficient quantity to generate a detectable signal if there is antibody in the sample capable of binding to the target antigen. The use of a purified target may decrease the possibility of a false positive signal due to antibody (whether autoantibody or other immunoglobulin) binding to contaminants in the antigen preparation. However, manufacturing the purified targets typically involves extensive biochemical purification from cellular extracts or of genetically engineered, recombinant proteins, each of which can be labor intensive and costly.

In contrast, the methods described herein use a crude cellular extract obtained from a cellular source known to contain most of the common autoantigens. In addition, this extract can be supplemented with individual autoantigens (e.g., chromatin, a common target of autoantibodies in certain autoimmune diseases) that might be deficient in the crude preparation. Thus, the targets for the assay described herein may be prepared inexpensively and rapidly compared to the production of recombinantly-produced and/or purified antigens. Thus, rather than detecting one or a small number of autoantibodies, the methods described herein can provide a broad screening of many disease-related autoantibodies simultaneously.

The methods described herein overcome the challenge of detecting antibody that is a tiny fraction of serum immunoglobulin in three ways. First, the crude cellular extract (with or without being supplemented with chromatin) includes numerous autoantigens that allows the device to capture multiple possible autoantibodies, increasing the chance that a positive signal will be generated, since patients commonly have several specificities that can vary from patient-to-patient. Second, the crude extract is irreversibly immobilized at high density on the assay membrane due to its high protein-binding properties and hydrophobic nature, enhancing its antibody-capturing capacity. Third, the biological sample is actively transported through the membrane, enhancing the rate and, therefore, probability of a productive antibody collision with the immobilized antigen.

The methods described herein reduce the frequency of false positive or high background results in at least two ways. First, the method involves detergents, inert carrier proteins and membrane blocking agents that suppress non-specific binding of immunoglobulins to the membrane, including, for example, bovine gamma globulin, bovine serum albumin, non-fat bovine total milk powder or casein, and/or animal gelatin such as from pig, cow or fish skin. Second, the membrane is washed during the assay with an excess of detergent-containing aqueous solution, drawn through the membrane by the application of negative pressure.

The crude extract that serves as the target for binding autoantibodies is typically a complex mixture of cellular proteins from a source known to express many common autoantigens. One exemplary source is an aqueous extract of rabbit thymus (RTE), the powder of which is commercially available from numerous sources (e.g., Immunovision, Inc., Springdale, Ak.; Enzo Life Sciences, Inc., Farmingdale, N.Y.; Santa Cruz Biotechnology, Inc., Dallas, Tex.). Other exemplary sources of suitable complex protein mixtures include, for example, any cultured human cell lines (for example HEp2, MALT4, HeLa, KB, etc.), animal tissue (mouse kidney, rat liver, rabbit and bovine thymus, etc.). These substrates are essentially an "array" presenting more than 100 autoantibody targets that may have differences in autoantigen content because of cell proliferation status, tissue of origin, etc. Immunologically-enriched sources (for example SS-A-transfected HEp2 cells) or cells arrested at specific time points of the cell cycle prior to harvesting can also be used. Alternatively, a mixture of purified native or recombinant proteins could be employed to produce a screening array of more limited or specific autoantibody target composition.

Figure 10:
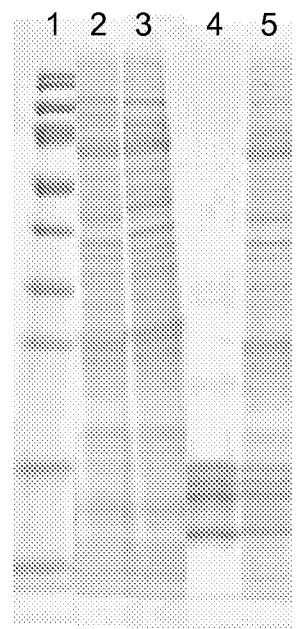
FIG. 10. SDS-PAGE analysis of exemplary complex target extract preparations. Lane #1: molecular weight markers; Lane #2: rabbit thymus extract; Lane #3: rabbit thymus extract; Lane #4: Hl-stripped chromatin; Lane #5: rabbit thymus extract from Lane #2 +Hl-stripped chromatin.
Figure 11:
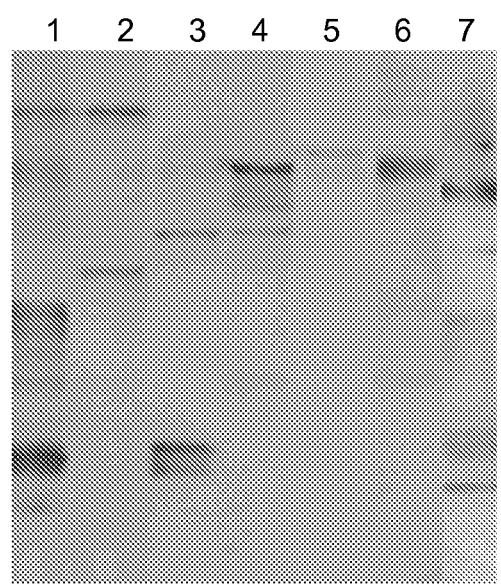
FIG. 11. Western Blot of RTE-chromatin (Lane #5, FIG. 10) analyzed with the indicated antibody. Lane #1: Anti-Smith antibodies (Sm); Lane #2: Anti-nuclear ribonucleoprotein antibodies (nuclear RNP); Lane #3: Anti-ribosomal ribonucleoprotein (ribosomal RNP); Lane #4: Anti-Ro (SS-A)/Anti-La (SS-B) antibodies; Lane#5: Anti-Jo-1 antibodies (Jo-1); Lane#6: Anti-Sc1-70 antibodies (Sc1-70); Lane #7: Anti-histone antibodies (histones). Prototype sera were derived from patients with rheumatic diseases and established as secondary standards for the indicated autoantibodies by demonstration of immunological identity with primary standard sera for that specificity, including sera obtained from the U.S. Centers for Disease Control.

In some cases, the complex target extract may be devoid of materials that can be autoantibody targets, risking a false-negative assay result. In these cases, the crude target extract can be supplemented with autoantigens such as H1-stripped chromatin, nucleosome core particles, myeloperoxidase, proteinase-3, mitochondrial, microsomal, and centromere antigens, cardiolipin or other phospholipids, RNA polymerase III, citrullinated antigens (cyclic citrullinated peptide) and the like. FIG. 10 shows SDS-PAGE analysis of the complex protein composition of RTE preparations with or without addition of chromatin. FIG. 11 shows Western Blot analysis of RTE+chromatin complex target extract probed with various autoantibodies, demonstrating its complex autoantigenic content. In the description that follows, unless otherwise expressly noted, the term "complex target extract" collectively includes embodiments either with or without supplementation with chromatin or other autoantigens.

Some sources of crude extract can, however, include antigens capable of binding human antibodies yet have no disease association. One example of this type of benign autoantibody target is the dense fine speckled antigen, which is lens epithelium-derived growth factor, LEDGF/p75. The presence of such an antigen in the crude extract can generate a false positive assay result. In embodiments that use such a source of crude extract to produce the complex target extract that is immobilized to the membrane, the method can include removing the benign antigen from the crude extract by any suitable method such as, for example, immunosorption.

The complex target extract can include a plurality of antigens designed to capture specific autoantibodies that are used to identify a variety of autoimmune disorders such as: Anti-Total Nuclear Antibody (ANA); Antineutrophil Cytoplamic Antibody (ANCA); Anti-Double Strand DNA (Anti-dsDNA); Anti-Sjorgren's Sydrome A (Anti-SS-A) (Ro); Anti-Sjogren's Sydrome B (Anti-SS-B) (La); Rheumatoid Factor (RF); Anti-Jo-1; Anti-Ribonuclear Protein (Anti-RNP); Anti-Smith (Anti-Sm); Antiscleroderma Antibody (Anti-scl-70); and Cardiolipin autoantibodies, as well as organ-specific autoantibodies such as: Thyroid Antibodies; Anti-Smooth Muscle Antibody (ASMA); Diabetes-associated Autoantibodies; Anti-Mitochondrial Antibody (AMA); and Liver-Kidney Microsomal autoantibodies. Accordingly, the complex target extract typically contains a plurality of autoantigens that specifically capture one or more of these autoantibodies. To reiterate, preferred embodiments of the method described herein use a complex target extract that includes a mixture of autoantigens that can be naturally prepared routinely and inexpensively from a crude cellular extract, minimizing the need to supplement the target mix with purified autoantigens.

Nevertheless, while occasionally described herein in the context of an exemplary embodiment in which the autoantibody being detected is total antinuclear antibodies, the devices and methods described herein can be designed to detect individually-specific autoantibodies or antibodies to any material in which a relatively pure antigen is available.

The complex target extract is immobilized to a membrane (e.g., by adsorption or any other suitable immobilizing method) that provides a porous substrate to which proteins in the target extract can bind and through which reagents may be drawn in order to perform the assay. The complex target extract may be immobilized at one or more zones in which the assay reactions will take place. Generally, the portion of the membrane to which the complex target extract is immobilized, and within which the assay reactions are performed may be termed a reaction zone. The reaction zone can include one area of immobilized complex target extract, within which one or more different samples, with or without controls, may be separately analyzed. Alternatively, the complex target extract may be "spotted" on multiple locations of the membrane within a general reaction zone, with a "spot" being the location of a single assay reaction.

The membrane may be constructed of any suitable material that possesses sufficient strength, irreversible high protein binding character, and microporosity. In some cases, the membrane may include poly(vinylidene (di)fluoride) (PVDF) obtainable from, for example, Millipore Corp., Bellerica, Mass.; Pall Life Sciences Corp., Port Washington, N.Y.; Pierce/Thermo Fisher Scientific, Rockford, Ill.) of 0.2-5.0 micron pore sizes.

Figure 13:
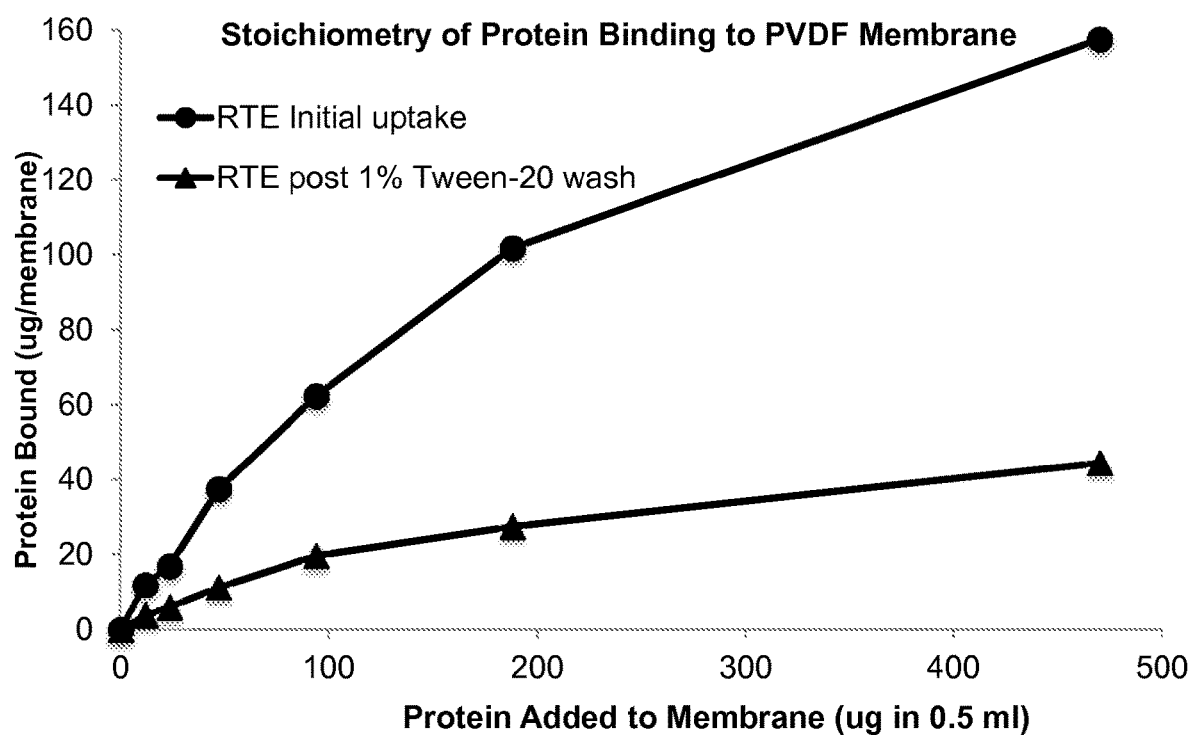
FIG. 13. Uptake of RTE on PVDF membrane. After initial uptake (binding) of RTE to membrane measured after saline wash, membranes were post-coated with 1% TWEEN-20 as performed in the standard membrane preparation step. The amount of membrane-associated protein was measured by BCA-colorimetric assay.
Figure 14A:
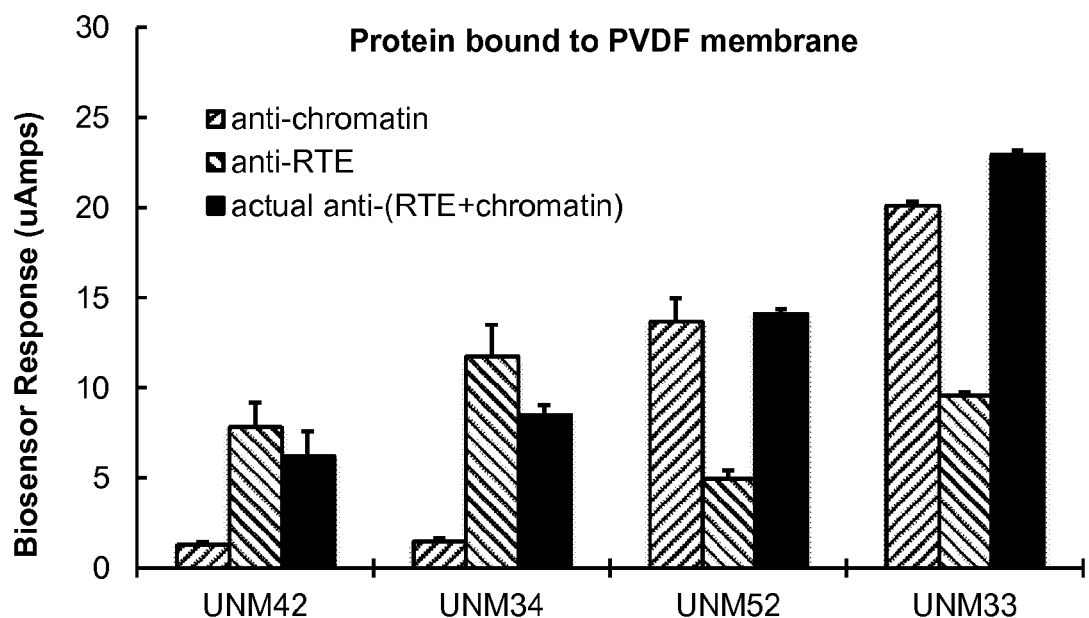
FIG. 14. Antigenic activity of RTE+/− chromatin using PVDF membrane in current sensor versus using polystyrene in the standard enzyme-linked immunosorbent assay (ELISA). (A) Four autoantibody-containing sera were tested in the current sensor for autoantibody binding to chromatin, RTE, and RTE+chromatin. (B) Four autoantibody-containing sera were tested by ELISA for autoantibody binding to chromatin, RTE, and RTE+chromatin.
Figure 14B:
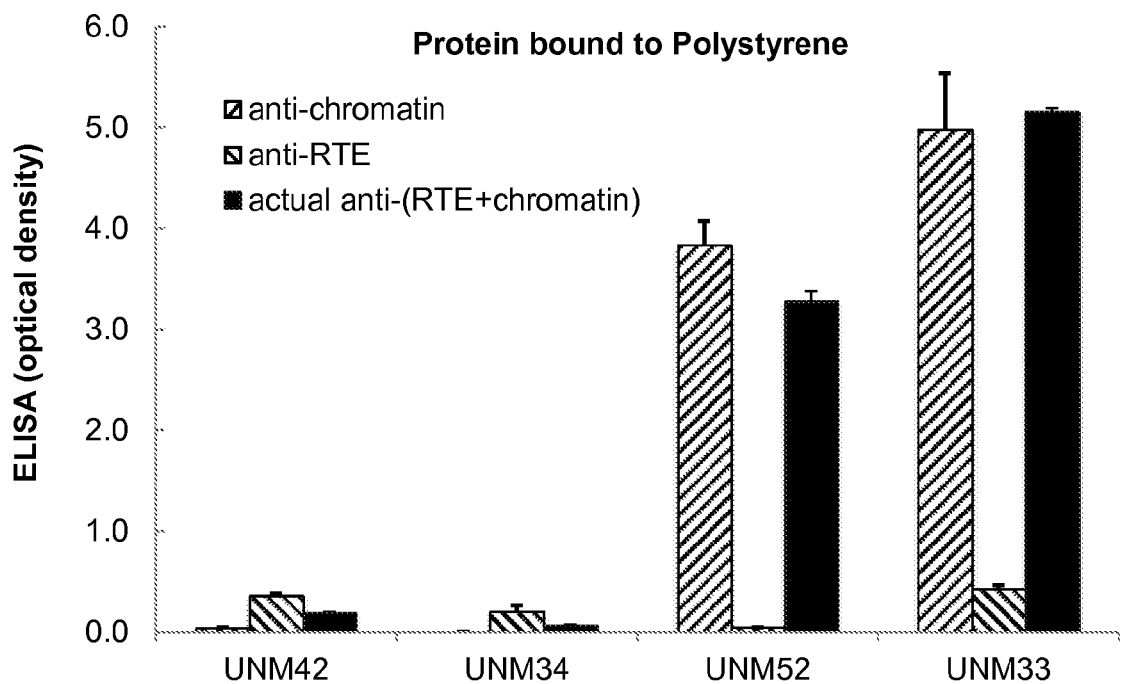

FIG. 13 shows that approximately 50% of added protein becomes bound to PVDF membrane with no clear saturation effect up to 400 µg/ml. Approximately 20% of this bound protein remains after incubation with 1% TWEEN-20. Therefore, at the standard membrane coating concentration of ~570 µg/ml, the 0.5 $cm^2$ immunoreaction-exposed area will have ~25 µg total protein. FIG. 14A shows that both anti-chromatin antibodies and anti-RTE antibodies were readily detected in all sera when using a PVDF membrane, and the mixture of chromatin+RTE under standard conditions resulted in only a 29% +/−6% decrease in total antibody activity compared to the sum of the individual activities. In contrast, as shown on FIG. 14B, in the standard ELISA anti-chromatin antibodies were detectable in only two of the four sera, anti-RTE antibodies were barely detectable, and the mixture of chromatin+RTE resulted in a 35% +/−30% decrease in total antibody activity. This difference in the sensitivity of the two assays reflects primarily the difference in the amount of protein antigen bound to the two types of solid phases: ~25 µg protein on PVDF membrane versus less than 0.5 µg protein on polystyrene.

The sample being tested may be any suitable biological sample that includes autoantibodies in a subject having or at risk of having an autoimmune condition. As used herein, the term "at risk" refers to a subject that may or may not actually possess the described risk. Thus, for example, a subject "at risk" of having an autoimmune condition is a subject possessing one or more risk factors associated with the condition such as, for example, genetic predisposition, ancestry, age, sex, geographical location, or medical history, even if the subject has not yet manifested any symptoms or clinical signs of the autoimmune condition. Typically, the biological sample can include blood or a blood product such as, for example, plasma or serum. Alternatively, however, the method may be performed using a biological sample that includes, for example, perspiration, saliva, urine, as well as pleural, pericardial and synovial fluids. Thus, while occasionally described herein in the context of an exemplary embodiment in which the biological sample is blood plasma, the devices and methods described herein can be designed to assay any of the biological samples listed immediately above.

The biological sample is contacted with at least a portion of the complex target extract in the reaction zone so that autoantibodies in the sample, if present, have an adequate opportunity to bind to autoantibody antigens in the immobilized complex target extract. This can involve drawing the sample through the membrane under negative pressure as described in more detail below.

The membrane is then washed with a detergent solution to remove unbound components of the biological sample—i.e., components of the biological sample that are not specifically bound to autoantigens that are immobilized to the membrane. In some cases, the membrane may be subjected to multiple washes. The detergent solution can include any suitable detergent such as, for example, polysorbate-20 (TWEEN-20, ICI Americas, Inc., Wilmington, Del.), polysorbate-80 (TWEEN-80, ICI Americas, Inc., Wilmington, Del.) or octylphenoxypolyethoxyethanol (NONIDET P-40; Shell Oil Co., Houston, Tex.). The wash may be performed by drawing the detergent solution through the membrane under negative pressure as described in more detail below.

After being washed, an anti-IgG antibody conjugated to an enzyme that catalyzes an electrode-detectable signal is contacted with at least a portion of the reaction zone so that the anti-IgG antibody has an adequate opportunity to bind to autoantibody (IgG) from the biological sample, if present, bound to autoantigen immobilized to the reaction zone of the membrane. This can involve drawing the anti-IgG antibody through the membrane under negative pressure as described in more detail below.

Figure 7:
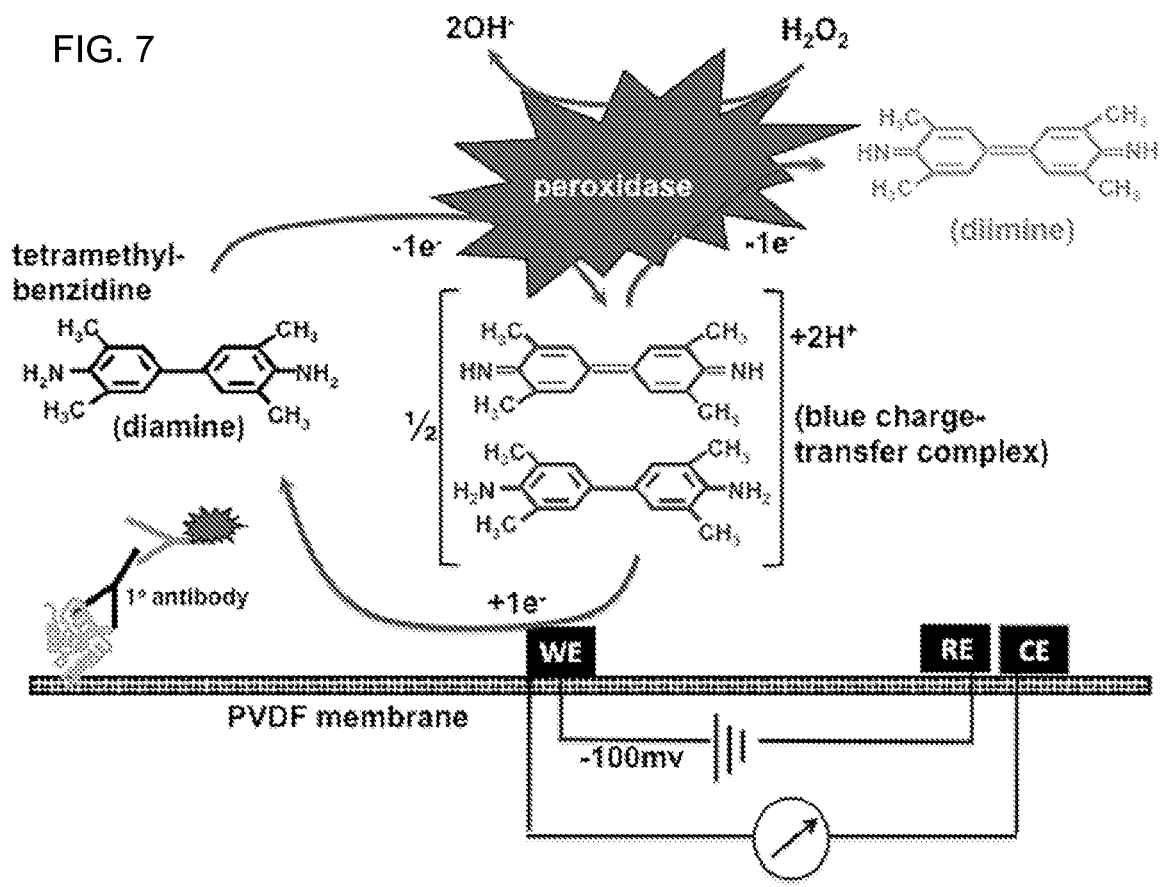
FIG. 7. The mechanism underlying an exemplary electrode-detectable signal for electrochemical detection of primary autoantibody bound to autoantigen immobilized on a PVDF membrane.

In some embodiments, the enzyme that catalyzes an electrode-detectable signal can be horseradish peroxidase, which can catalyze conversion of the secondary substrate 3,3',5,5'-tetramethylbenzidine (TMB) to the diimine charge transfer complex intermediate, which can be measured at the microamperage level by electrodes, as shown in FIG. 7. Other possible enzymes that can catalyze an electrode-detectable signal include, for example, myeloperoxidase (which catalyzes the production of hypochlorous acid, HOCl, from hydrogen peroxide, $H_2O_2$ and chloride anion, $Cl^-$) and alkaline phosphatase (which catalyzes the conversion of para-nitrophenol phosphate to para-nitrophenol). Thus, while occasionally described herein in the context of an exemplary embodiment in which the enzyme is horseradish peroxidase, the devices and methods described herein can be designed to include any enzyme capable of catalyzing an electrode-detectable signal including those enzymes expressly identified immediately above.

The membrane is then washed again with a detergent solution to remove unbound anti-IgG antibody. In some cases, the membrane may be subjected to multiple washes. The detergent solution can include any suitable detergent such as, for example, TWEEN-20, TWEEN-80, NONIDET P-40. The wash may be performed by drawing the detergent solution through the membrane under negative pressure as described in more detail below.

Finally, electrodes are positioned to detect the electrode-detectable signal—e.g., the unstable TMB semiquinone diimine cation free radical (FIG. 7) as it forms in the reaction zone after enzyme secondary substrate TMB and primary substrate hydrogen peroxide are contacted with the reaction zone where peroxidase/anti-human IgG antibody is bound to the membrane. An amperometric signal is generated by the electrochemical reduction of the TMB intermediate using the electrodes, as illustrated in FIG. 7.

In the preceding summary of the method, many steps involve drawing a fluid through the membrane. Generally, a fluid—whether a patient sample, a wash, or a reagent—may be drawn through the membrane at a minimum rate of 0.001 ml/min such as, for example, at least 0.01 ml/min, at least 0.05 ml/min, at least 0.08 ml/min, at least 0.1 ml/min, at least 2.0 ml/min, at least 0.5 ml/min, at least 0.7 ml/min, or at least 1.0 ml/min. A fluid may be drawn through the membrane at a maximum rate of 10 ml/min such as, for example, no more than 5.0 ml/min, no more than 1.0 ml/min, no more than 0.8 ml/min, no more than 0.7 ml/min, no more than 0.5 ml/min, no more than 0.2 ml/min, no more than 1.0 ml/min, or no more than 0.8 ml/min. A fluid may be drawn through the membrane at a rate having endpoints defined by any minimum rate listed above and any maximum rate that is greater than the minimum rate.

Accordingly, a fluid may be drawn through the membrane for a minimum period of 10 second such as, for example, at least 20 seconds, at least 30 seconds, at least one minute, at least two minutes, at least 2.5 minutes, at least three minutes, or at least five minutes. A fluid may be drawn through the membrane for a maximum period of 10 minutes such as, for example, no more than five minutes, no more than three minutes, no more than two minutes, no more than one minute, or no more than 30 seconds. A fluid may be drawn through the membrane for a period having endpoints defined by any minimum period of time listed above and any maximum period of time that is greater than the minimum period of time.

In one exemplary embodiment, using the device illustrated in FIG. 12, the biological sample may be drawn through the membrane at a rate of 0.08 ml/min for approximately 2.5 minutes, the detergent solution may be drawn through the membrane at a rate of 0.7-1.0 ml/min for approximately 30 seconds, the anti-IgG antibody may be drawn through the membrane at a rate of 0.2 ml/min for approximately one minute, and the detergent solution again may be drawn through the membrane at a rate of 0.7-1.0 ml/min for approximately 30 seconds.

As discussed above, the biological sample is actively transported through the membrane, enhancing the rate and, therefore, probability of a productive antibody collision with the immobilized antigen. Thus, in some embodiments, the method may be completed during the brief time a patient remains in the clinic, making it feasible to use as a point-of-care diagnostic aid. Accordingly, in some embodiments, the method may be performed in a maximum of 60 minutes such as, for example, no more than 45 minutes, no more than 30 minutes, no more than 25 minutes, no more than 20 minutes, or no more than 15 minutes.

Devices

Figure 8:
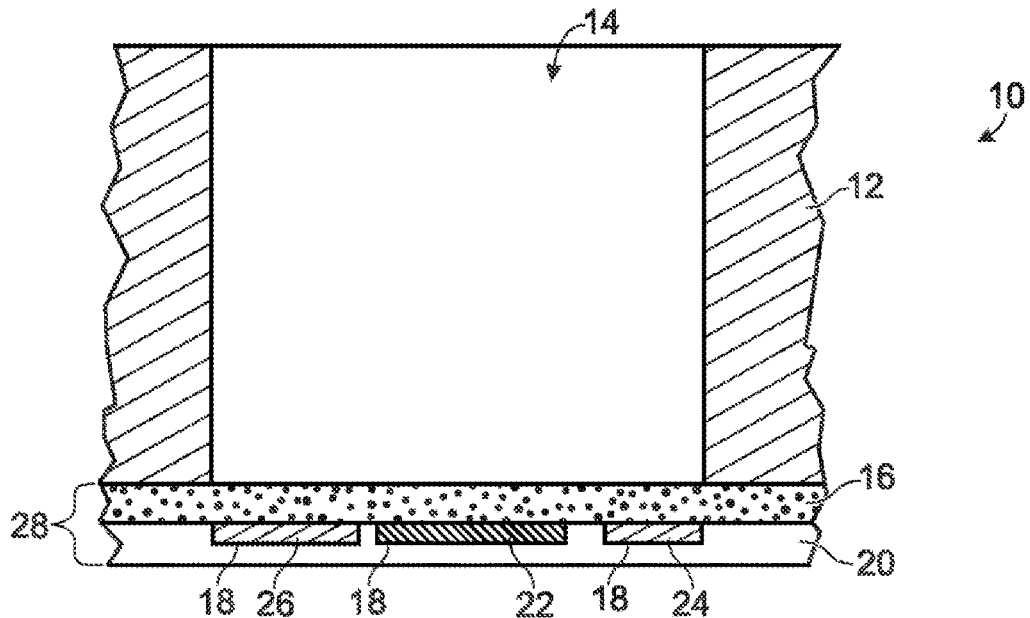
FIG. 8. A schematic illustration of a single well flow-through electrochemical immunoassay detection unit.
Figure 9:
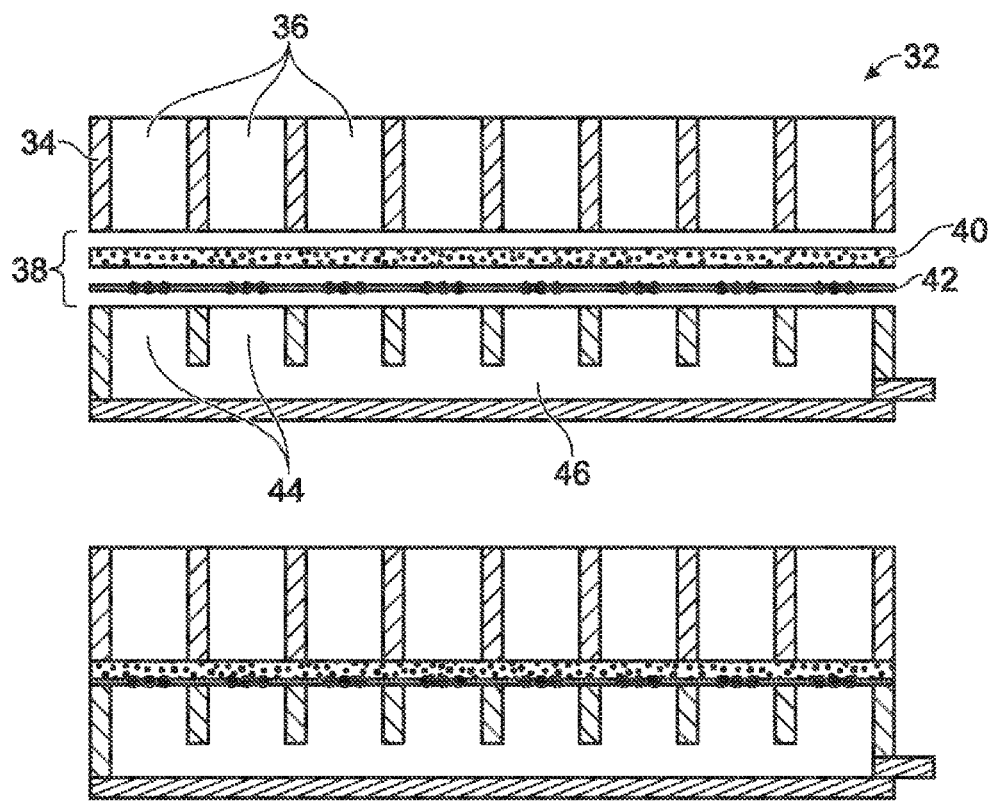
FIG. 9. A schematic illustration of the multiplexed flow-through immunosensor assembly illustrated in FIG. 3. (A) an exploded view of the sensor; (B) depicts the assembled sensor.

One embodiment of a device 10 designed to perform the method described above is shown in FIG. 3 and illustrated in FIG. 8 and FIG. 9. The sensor can include a body 12 including a channel 14 into which the sample may be introduced. As shown, within channel 14 is a porous membrane 16 which, in turn, is in fluid contact with an electrode assembly 18 connected to an amperometric strip reader (not shown). Electrode assembly 18 may include, for example, a substrate 20 having a working electrode 22, a reference electrode 24, and a counter electrode 26. According to some embodiments, electrodes 22, 24, and 26 may be screen-printed, etched, plated, or layered, using then-film technologies, onto substrate 20. In combination, the porous membrane 16 and electrode assembly 18 form a reaction zone 28. When reagents are drawn from the channel 14 through the reaction zone 28, a variety of interactions, reactions, and/or detections may take place. A source of negative pressure (not shown), such as, for example, a vacuum is provided in fluid communication with the reaction zone 28 and opposite from the channel 14. The source of negative pressure may draw fluid deposited in channel 14 through and across the porous membrane 16.

FIG. 9 provides an alternate fluid flow device 32 that reflects a multi-channel flow-through system. FIG. 9A shows an exploded view of the device, while FIG. 9B shows the assembled device. In this device, a single housing 34 defines multiple channels 36. The device includes a reaction zone 38 that, collectively, includes a porous membrane 40 and an electrode assembly 42. As with the device shown in FIG. 8, each electrode assembly may include a working, reference, and counter electrode. Also as in the device shown in FIG. 8, a source of negative pressure (not shown) is provided in fluid communication with the reaction zone 38 and opposite from the channels 36. The porous membrane 40 may have a plurality of antigens immobilized to the membrane for capturing autoantibody that may be present in the biological sample that is introduced into the channel 36.

In a multi-channel embodiment such as is illustrated in FIG. 9, the capture antigens associated with each channel 36 may be the same as or different than the capture antigens associate with other channels 36 in the device. For example, a different complex target extract may be immobilized to the porous membrane 40 in different channels in order to screen a single patient sample against a broader spectrum of autoantigens. Alternatively, the same complex target extract may be immobilized to the porous membrane 40 in multiple channels so that multiple samples, in some cases from multiple subjects, may be analyzed simultaneously.

Figure 12A:
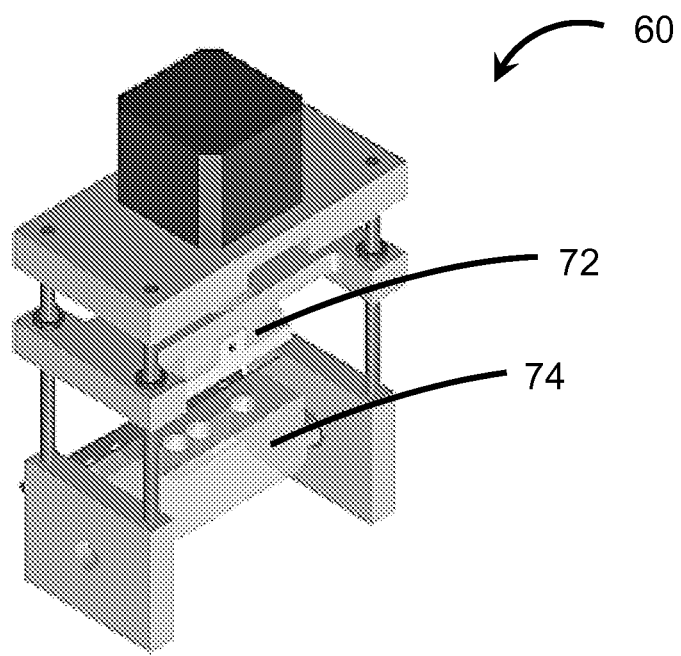
FIG. 12. (A) A top perspective view of a three-chambered embodiment of a device as described herein. (B) A bottom perspective view of the three-chambered embodiment of the device.
Figure 12B:
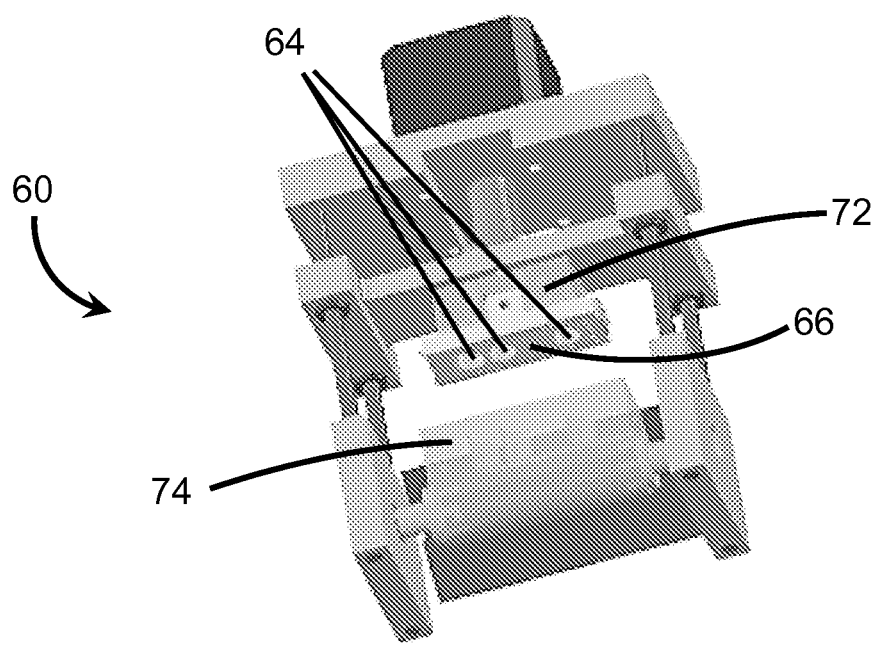

In another embodiment, illustrated in FIG. 12A and FIG. 12B, the device 60 may have three channels 64: one channel for analyzing a biological sample, a channel dedicated for a negative control, and a third channel dedicated for a positive control. In the illustrated embodiment, an upper manifold 72 is provided for delivering sample to the channels 64. The porous membrane 66 is shown in FIG. 12B clamped to the upper manifold 72.

In one particular embodiment of using the device, a biological sample is added to the analyzing channel, while a control diluent is added to the positive control channel and the negative control channel. When fluid—whether biological sample, control diluent, wash solution, or reagent solution—is to be drawn through the porous membrane 66, the upper manifold 72 may be lowered to contact the lower manifold 74, which is in fluid communication with a source of negative pressure (not shown). When negative pressure is created, the fluid is drawn from the upper manifold 72 through the porous membrane 66, and into the lower manifold 74. The biological sample and control diluents are evacuated at a rate of 0.08 ml/min under a vacuum for about 2.5 minutes. Each channel is subsequently washed twice with a detergent solution to remove components of the biological sample that have not bound to the membrane.

After each wash, each channel is evacuated at a rate of 0.7-1.0 ml/min under a vacuum for about 30 seconds. Anti-IgG antibody (conjugated to an enzyme that can catalyze an electrode-detectable signal) is added to each channel and allowed to react with IgG that is bound to the membrane. Fluid is evacuated from each channel at a rate of 0.2 ml/min under a vacuum for about one minute. Each channel is then once again washed twice with a detergent solution to remove unbound anti-IgG antibody. After each wash, each channel is evacuated at a rate of 0.7-1.0 ml/min under a vacuum for about 30 seconds.

To detect the electrode-detectable signal, an electrode assembly may be placed on the lower manifold 74 before the upper manifold is lowered and the reagent solution added via channels 64. In this measurement position, the electrode assembly contacts the reaction zone of the membrane so that one individually-addressable electrode contacts the reaction zone of the membrane corresponding to one channel. In some embodiments, the electrode assembly may be attached to a rotatable platform onto which the electrode assembly may be loaded from the side of the device 60, then rotated so that the platform positions the electrode assembly over the lower manifold 74 into the measurement position.

With the electrode assembly in the measurement position, the measuring reagent is added to each channel and allowed to contact the membrane for 10 minutes. After the 10-minute incubation, −100 mv is applied to each channel for a pulse of 5 milliseconds every 200 milliseconds for 20 pulses. Measurements are taken from the electrode near the end of each pulse. Each channel is pulses and measured independently. The final 15 measurements from each channel are averaged and displayed.

In particular, the device illustrated in FIG. 12 provides a portable, field-usable form of the device that can analyze a biological sample from a patient and provide a result while a patient remains in the clinic. Thus, this embodiment of the device is particularly suited for use as a point-of-care diagnostic aid.

According to some embodiments, the molecules of interest may be antinuclear antibodies associated with autoimmune diseases or other diseases with an autoimmune component (Table 1).

TABLE 1

Autoimmune serology assessment for possible rheumatic disease in emergency settings

| Symptom | Positive Test Result | Disease |
| --- | --- | --- |
| Airway symptoms | | |
| Hemoptysis | Anti-dsDNA, other lupus serologies | Alveolar hemorrhage in SLE |
| Airflow obstruction | Anti-CCP, RF | Cryoarytenoid arthritis in rheumatoid arthritis (AR) |
| Mucopurulent rhinorrhea; subglottic stenosis; hypopharyngeal ulcerations | Anti-neutrophil cytoplasmic Antibodies (ANCA, MPO, or PR3) | Wegener's granulomatosis |
| Stridor, laryngeal strictures | Anti-type II collagen | Relapsing polychondritis |
| Acute pneumonitis | Anti-dsDNA, other lupus serologies | SLE |
| Pulmonary-renal symptoms | | |
| Pulmonary hemorrhage and acute renal failure | Anti-GBM, MPO-ANCA, PR3-ANCA | Goodpasture's syndrome; systemic vasculitis |
| Neuropsychiatric symptoms | | |
| Encephalopathy, psychosis, focal central nervous system disease | Anti-N-methyl-D-aspartate receptor (NMDA-R), anti-ribosomal P antibodies, anti-phospholipid antibodies | Neuropsychiatric SLE, anti-phospholipid syndrome |
| Weakness, paralysis, bilateral sensory deficit, impaired sphincter control | Lupus serologies | Transverse myelitis in SLE |
| Seizures | Anti-dsDNA, other lupus serologies | Lupus cerebritis |
| Thromboembolic symptoms | | |
| DVT, pulmonary thromboembolism, fetal loss, retinal artery occlusion | Anti-phospholipid antibodies | Anti-phospholipid syndrome |
| Neuromuscular symptoms | | |
| Progressive symmetric muscle weakness, dysphagia, dysphonia | Anti-Jo-1, other myositis-specific antibodies | Dermatomyositis, polymyositis |
| Unusual weakness and hypokalemia | Anti-Ro/SSA, anti-La/SSB | Sjogren's syndrome hypokalemic paralysis |
| Cardiac symptoms | | |
| Pleuritic or positional chest pain, dyspnea, tachycardia | Anti-dsDNA, other lupus serologies | SLE pleuro-pericarditis, pericardial tamponade |
| Congenital heart block, neonatal carditis | Anti-Ro/SSA, anti-La/SSB | Neonatal SLE |
| Renal symptoms | | |
| Rapidly progressive renal failure | MPO-ANCA, PR3-ANCA, anti-dsDNA and other lupus serologies, anti-phospholipid antibodies | Microscopic polyangiitis, WG, lupus nephritis, catastrophic anti-phospholipid syndrome |
| Accelerated hypertension | Anti-Scl-70, anti-centromeres, anti-RNA-Polymerase III | Renal crisis in systemic sclerosis |
| Joint symptoms | | |
| Pain, stiffness, swelling with symptoms of systemic disease | Anti-CCP, RF, and lupus serologies | RA, SLE |

TABLE 1-continued

Autoimmune serology assessment for possible rheumatic disease in emergency settings

| Symptom | Positive Test Result | Disease |
|---|---|---|
| Ocular symptoms | | |
| Red, painful, photophobic eye | RF, anti-CCP, lupus serologies | RA, Behcet's, juvenile RA, SLE |
| Gastrointestinal symptoms | | |
| Colicky abdominal pain | Lupus serologies | SLE mesenteric arteritis |
| Skin symptoms | | |
| Petechiae, palpable purpura, hemorrhagic blisters, ulcerations and gangrene | SLE and RA serologies | SLE, rheumatoid vasculitis |
| Neonatal skin rash | Anti-Ro/SSA, anti-La/SSB | Neonatal lupus |
| Hematological symptoms | | |
| Anemia, thrombocytopenia, leukopenia | Anti-DNA and lupus serologies, anti-erythrocyte, anti-platelet antibodies | SLE, autoimmune hemolytic anemia |
| Thrombocytopenia | Anti-phospholipid antibodies | Anti-phospholipid syndrome |

ANCA: anti-neutrophil cytoplasmic antibodies
CCP: cyclic citrullinated peptide
DVT: deep venous thrombosis
GBM: glomerular basement membrane
MPO: myeloperoxidase
NMDA-R: N-methyl-D-aspartate receptor
PR3: proteinase 3
RA: rheumatoid arthritis
RF: rheumatoid factor
SLE: systemic lupus erythematosus Some of the autoantibodies listed in Table 1 as diagnostic aids can increase or decrease with disease activity, and may therefore provide prognostic clinical information to guide therapy for a variety of rheumatic diseases. When target organ involvement is considered, autoantibodies may correlate with clinical outcomes. Exemplary candidate autoantibody disease activity markers are summarized in Table 2. Accordingly, the devices disclosed herein may be used to detect, monitor, and/or quantify, a wide variety of molecules of interest including the autoantibodies shown in Tables 1 and 2.

TABLE 2

Associations between autoantibody changes and disease activity

| Disease/Condition | Autoantibody | Change | Clinical Outcome |
|---|---|---|---|
| Systemic lupus erythematosus | Anti-dsDNA | Increase | Active flare |
| | Anti-dsDNA | Decrease | Active flare |
| | Anti-nucleosome | Increase | Active disease/lupus nephritis |
| | Anti-C1q | Increase | Lupus nephritis/active disease |
| | Anti-NMDA-R | Increase | Permanent CNS impairment |
| | Anti-NMDA-R | Decrease | Transient CNS symptoms |
| | Anti-CRP | Increase | Lupus nephritis/response to therapy |
| | Anti-interferon-α | Decrease | Inactive disease |
| Systemic vasculitis | Anti-PR3 | Increase | Active disease/disease relapse |
| | Anti-MPO | Increase | Active disease/disease relapse |
| | Anti-GBM | Increase | Active disease/disease relapse |
| Scleroderma | Anti-topoisomerase I | Increase | Active scleroderma |
| Rheumatoid arthritis | Anti-drug (adalimumab) | Increase | Treatment failure |
| Anti-phospholipid syndrome/SLE | Anti-phospholipid | Increase | Procoagulant state, thrombosis |
| Necrotizing myopathy | Anti-signal recognition particle | Increase | Decreased muscle strength, increased creatine kinase activity |
| Thrombotic thrombocytopenic purpura | Anti-ADAMTS13 antibodies | Increase | Disease relapse |
| Pregnancy in SLE | Anti-Ro(SSA)/anti-Ro52 | Increase | Congenital heart block |
| | Anti-La(SSB) | Increase | Neonatal lupus |

TABLE 2-continued

Associations between autoantibody changes and disease activity

| Disease/Condition | Autoantibody | Change | Clinical Outcome |
|---|---|---|---|
| Autoantibody serum screening | Anti-DFS70 | Increase | ANA-positive healthy individuals |

ADAMTS13: a desintegrin and metalloproteinase with a trombospondin type 1 motif, member 13
CRP: C-reactive protein
DFS70: dense fine speckles 70 kDa
GBM: glomerular basement membrane
MPO: myeloperoxidase
NMDA-R: N-methyl-D-aspartate receptor
PR3: proteinase 3
SLE: systemic lupus erythematosus In the preceding description, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Figure 2:
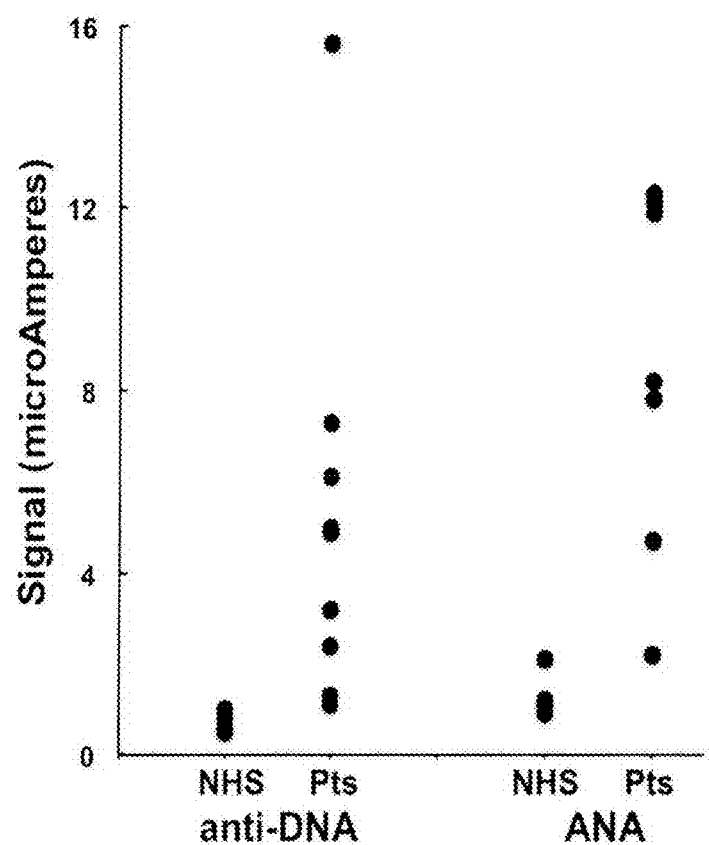
FIG. 2. Results of tests using the biosensor of FIG. 1.

Eight diluted serum samples were simultaneously drawn through the membrane of the device shown in FIG. 1 by weak vacuum, and bound IgG was detected with an anti-IgG peroxidase conjugate. The electrochemical reduction of the oxidation product of peroxidase action on TMB on top of the independently addressable electrode sets placed beneath the membrane was recorded in microamperes. FIG. 2 shows typical signal output generated at 13 minutes by normal human sera (NHS) or SLE sera (Pts) with various ANA or anti-dsDNA levels. The electrochemical assay for anti-DNA compared favorably with standard ELISA and showed a high degree of correlation (r=0.9) with very similar limit of detection. (Rubin et al., 2014, *Biosensors and Bioelectronics*, 51:177-183).

The data shown in FIG. 2 indicate that this electrochemical biosensor could be used as a POC device for measuring autoantibodies by virtue of its fast processing time, use of inexpensive materials, reagents and electronics.

Example 2

Human Serum Samples

Blood was obtained from donors under auspices of a human subjects protocol approved by the institutional human research review committee. After clotting, serum was removed by centrifugation and stored at 5° C. in the presence of 0.05% sodium azide for <6 weeks prior to use. Blood from patients diagnosed with various autoimmune diseases was used for ANA positive samples. Donors of normal blood were anonymous employees of the university.

Autoantigens preparation

Rabbit thymus acetone powder (Immunovision RTP-1000, Springdale Ariz.) was suspended in cold phosphate buffered saline (PBS, 0.14M NaCl, 0.01M Na phosphate, pH 7.4) at a ratio of 2 g per 30 ml (67 mg/ml), and 5 mg phenylmethylsulfonyl fluoride (Sigma-Aldrich, St. Louis, Mo.) was added. The mixture was stirred at moderate rate overnight at 5° C. After centrifugation at 3000 RPM for 10 min, the supernatant was re-centrifuged at 10,000 RPM for 60 minutes. This slightly turbid rabbit thymus extract (RTE) had a protein content of ~4.0 mg/ml (BCA assay, Pierce Biotechnology, Thermo Fisher Scientific, Inc., Rockford, Ill.), and was stored in 1.0 ml aliquots at −70° C. Chromatin (chr) was purified from calf thymus based on Lutter, L. C., 1978. J. Mol. Biol. 124, 391-420 and stripped of histone H1 as described previously. (Burlingame, R. W., and Rubin, R. L., 1990. *J Immunol Methods* 134, 187-199; Burlingame, R. W., and Rubin, R. L., 2002. In: Rose, N. R., Hamilton, R. G., Detric, B. (Eds.), Manual of Clinical Laboratory Immunology, pp. 951-960, 6th ed. American Society for Microbiology, Washington, D.C.). The concentration of its DNA component was determined by absorbance at 260 nm based on E=25 for 1 mg/ml, and its protein content was determined by the BCA assay. Protein/DNA ratio of the chromatin preparations was ~1.27. It was stored in liquid form in 50% glycerol at −20° C. at a concentration of ~0.3 mg DNA/ml.

Autoantigen-Coated Membrane for Immunosensor

A sheet of polyvinylidene (di)fluoride (PVDF) membrane (0.45 μm pore size, Pall Life Sciences Corp., Port Washington, N.Y.) is cut into 1.0 cm×8.25 cm strips for the purpose of simultaneously testing 8 samples (see below). Just before coating, each strip is placed in an individual 13 mm×100 mm glass test tube and hydrated by sequential immersion in methanol, 25% methanol, water, and then PBS with 0.01% thimerosol. For autoantigen coating of membrane, 1.0 ml (3.8-4.3 mg) rabbit thymus extract (RTE) and 0.62 ml (0.17 mg) chromatin is diluted to 8.0 ml in cold PBS (RTE/ chromatin ratio=~25). After continuous tube inversion for five minutes, the membrane is incubated overnight at 5° C., rinsed with PBS/thimerosol and immersed in a solution of 0.1% bovine serum albumin (BSA, Sigma-Aldrich, St. Louis, Mo.), 1.0% TWEEN-20 (polyoxyethylene sorbitan monolaurate, stabilized and peroxide/aldehyde-free, Sigma-Aldrich, St. Louis, Mo.) in PBS for two hours at room temperature. This post-coating stage is followed by rinsing the membranes in PBS and replacing it with membrane "wash solution" of 0.005% NP-40 (Sigma-Aldrich, St. Louis, Mo.) in PBS/thimerosol. Membranes were either used the same day or stored at 5° C. in wash solution. Based on the direct measurement of membrane-bound protein, 35 µg protein was stably bound to 0.5 $cm^2$ well-exposed membrane.

Immunosensor Design

Figure 3:
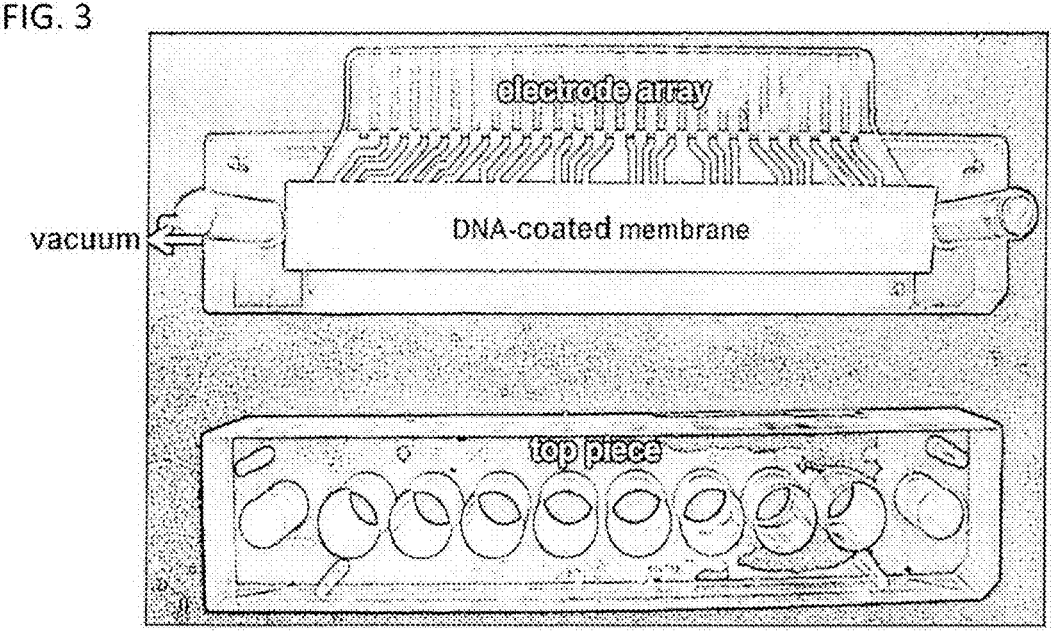
FIG. 3. An alternative embodiment of a flow-through device for measuring autoantibodies, for example anti-DNA antibodies, in eight samples. The fully assembled apparatus, in which the top piece is placed over the membrane coated with, for example, DNA (or any antigen or antigen mixture), is sealed with a gasket and wing nuts on the threaded posts. The electrode array would be inserted under the membrane after the primary and secondary antibodies are drawn and washed through the membrane using a weak vacuum applied below the membrane through the lucite bottom piece.

An 8-well manifold was machined in two parts from stabilized acrylic as shown in FIG. 3. Each well had a diameter 0.8 cm, exposing 0.5 $cm^2$ of the underlying membrane. Below the membrane was placed another acrylic block with eight cavities aligned with those in the top piece. A gasket was inserted at the interface between the membrane and the top piece, which was sealed to the bottom piece by wing nuts tighten onto two threaded posts separated by 8.25 cm. Perpendicular to the walls of all the wells in the bottom piece was drilled a 1 mm diameter channel, exiting through a stainless-steel hollow rod to which a vacuum can be applied. During the immunoassay after the final wash step (see below), the apparatus was disassembled and a plastic strip containing eight independently-addressable electrode sets (Alderon Biosciences, Inc., Beaufort, N.C.) was aligned with the cavities in the bottom piece with the aid of alignment rods inserted into holes drilled through the plastic strip containing the electrode sets. Each electrode set consisted of a central working carbon graphite electrode surrounded by a carbon graphite electrode and a silver chloride reference electrode within a 0.8 cm diameter, and at a 0.9 cm center-to-center separation from the adjacent set(s). The immunoreactant-exposed membrane was aligned with the electrode, and the top piece was sealed to the bottom piece as described above. The electrode terminals were connected through a cable to an amperometric reader (Alderon Biosciences, Inc., Beaufort, N.C.), whose parameter settings were controlled and output monitored by interface with a computer using the manufacturer's software.

Amperometric Immunoassay

All steps were performed at room temperature. The test sera were diluted 1:50 in ultrafiltered "serum diluent" consisting of 2.5 mg/ml bovine gamma globulin (BGG, Calbiochem EMD Biosciences) and 3.5 mg/ml BSA in "wash solution". After assembly of the apparatus with the antigen-coated membrane, each of the eight wells was loaded with 0.2 ml diluted human serum, and the samples were simultaneously drawn through the membrane over the course of 2.5 minutes at 0.08 ml/min using a weak vacuum applied to the lower channel by a peristaltic pump (W-M Alitea AB, Stockholm, Sweden). Each well was then rinsed with 0.1 ml and then 0.4 ml wash solution. Then, 0.2 ml peroxidase-conjugated rabbit anti-human IgG (SouthernBiotech, Birmingham, Ala.) diluted 1:10,000 in "serum diluent" was drawn through the membrane at 0.2 ml/min followed by three sequential rinses with 0.1 ml, 0.4 ml, and then 0.4 ml wash solution at 0.7 ml/min. After inserting the electrode array, 0.15 ml peroxidase substrate solution consisting of commercially-stabilized hydrogen peroxide ($H_2O_2$)+2 mM 3,3',5,5' tetramethylbenzidine ("TMB liquid substrate system", Sigma-Aldrich, St. Louis, Mo.) was added to each well. Beginning at 1 minute, intermittent pulse amperometry is employed at two-minute intervals at a potential of −100 mV by using twenty 5 msec voltage pulses over the course of four seconds.

Each displayed time point represents the average current of the last fifteen 5 msec pulses. Total time for manipulation and washing of each sample required about six minutes plus 7-13 minutes for product development for a total elapsed time from addition of serum to readout of approximately 20 minutes.

Figure 4:
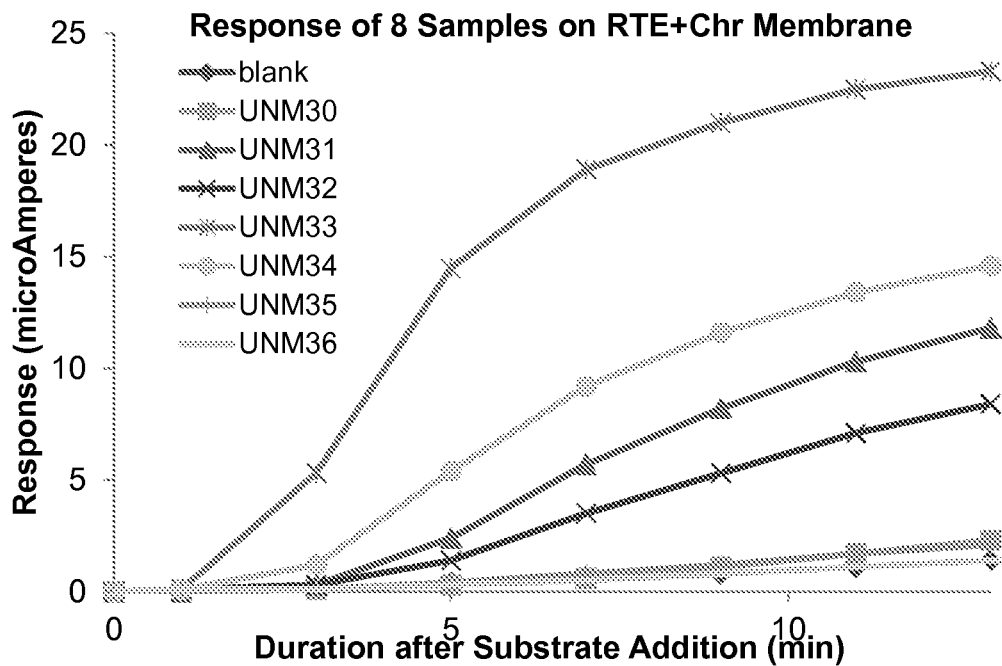
FIG. 4. The kinetic response of eight samples on RTE+Chr (rabbit thymus extract+chromatin) membrane.
Figure 5:
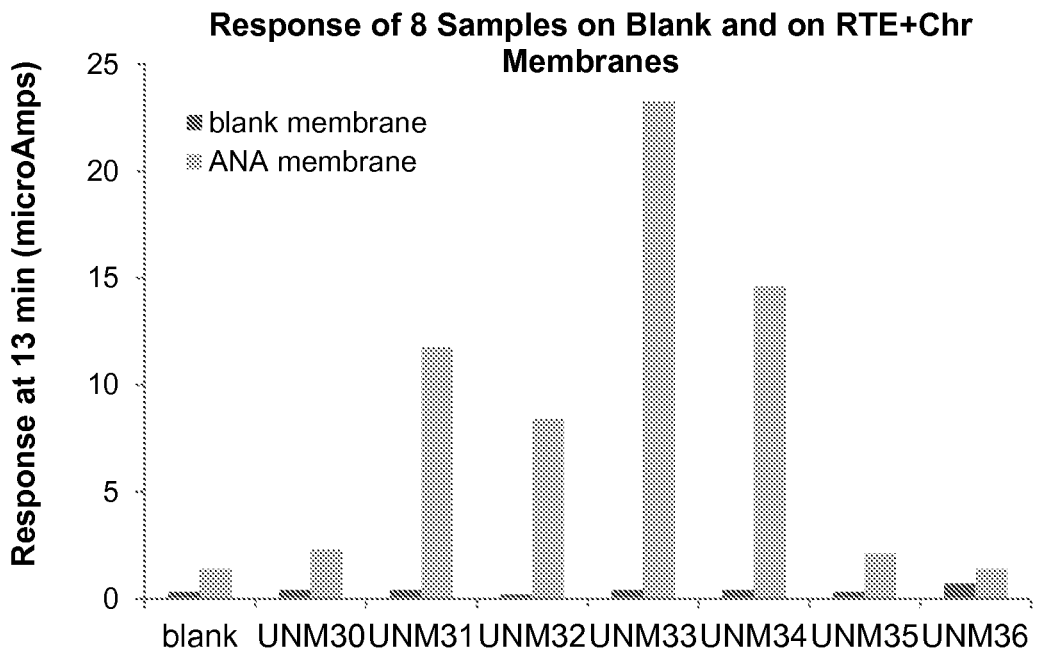
FIG. 5. The response at 13 minutes of eight samples on blank and on RTE+Chr (rabbit thymus extract+chromatin) membranes.

Results are shown in FIG. 4 and FIG. 5.

Example 3

Figure 6:
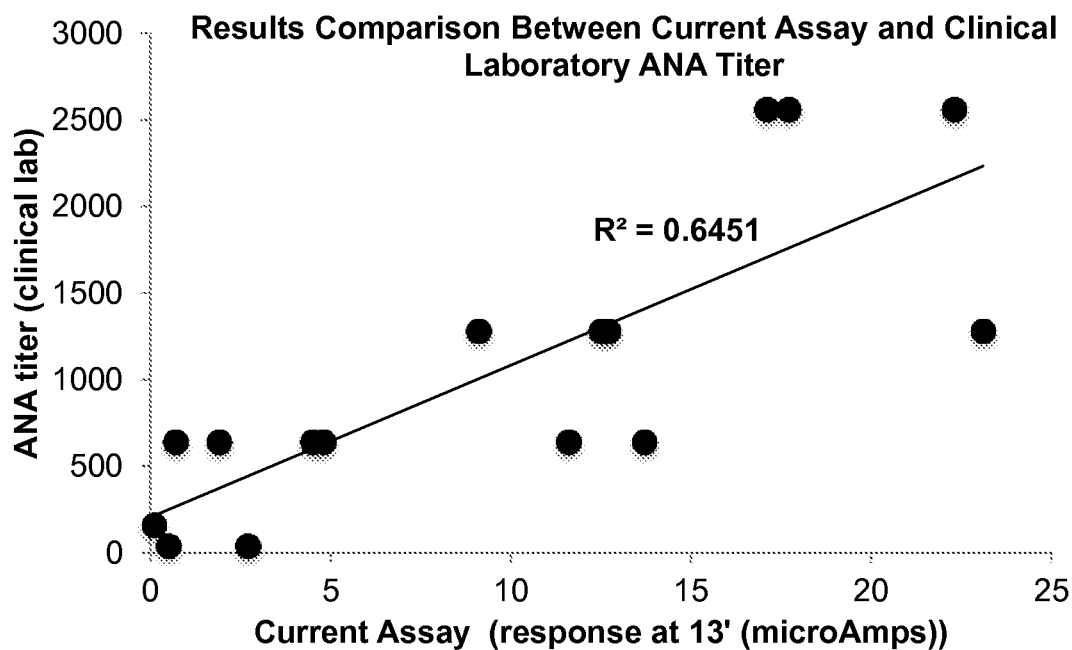
FIG. 6. A comparison between current assay and clinical laboratory ANA titer.

The 8-well sensor illustrated in FIG. 1 was used to measure ANA electrochemically as described in Example 2 with the inclusion of more sera from different patient samples. FIG. 6 compares the ANA activity as measured by the sensor shown in FIG. 1 with the corresponding ANA titer as reported by the clinical laboratory. ANA titer was determined through Tricore Reference Laboratories based on Fritzler, M. J., Immunofluorescence antinuclear antibody tests, 1997 In: Rose, N. R., de Marcario, E. C., Folds, J. D., Lane, H. C., and Nakamura, R. M., Manual of Clinical Laboratory Immunology, pp. 920-927, 5th ed. American Society for Microbiology, Washington, D.C. using serum from the same patients used in the "Current Assay", which was performed as described in Example 2.

Blood was obtained from donors under auspices of a human subjects protocol approved by the institutional human research review committee. The donors in this example were different than the donors who provided samples in Example 2.

Example 4

Sodium dodecyl sulfate (SDS)-polyacrylamide gel electrophoresis (PAGE) and subsequent Western blot were performed based on the methods of Laemmli, U. K., 1970, Nature 227, 680-685 and of Towbin, H., Staehelin, T, and Gordon, J., 1979, Proc. Nat. Acad. Sci. USA 76, 4350-4354, respectively, as described in Chan, E. K. L and Pollard, K. M., Detection of autoantibodies to ribonucleoprotein particles by immunoblotting, 1997 In: Rose, N. R., de Marcario, E. C., Folds, J. D., Lane, H. C., and Nakamura, R. M., Manual of Clinical Laboratory Immunology, pp. 928-934, 5th ed. American Society for Microbiology, Washington, D.C.

The stained SDS-PAGE and the Western blot gels were 15% polyacrylamide. RTE3 and RTE4 were two independent lots of aqueous extracts of rabbit thymus acetone powder (Immunovision, Inc., Springdale, Ak.) prepared as described in the "Autoantigens preparation" section of Example 2, above. H1-stripped chromatin was prepared as described in in the "Autoantigens preparation" section of Example 2, above.

In FIG. 10, the protein loaded in Lane 2 was 21 µg RTE4; Lane 3 was 22 µg RTE3; Lane 4 was 4 µg H1-stripped chromatin; and Lane 5 was 19 µg RTE4+1.5 µg chromatin.

In FIG. 11, each lane contained 12 µg RTE4+1 µg chromatin. Probe antibodies: Lane #1: Anti-Smith antibodies (Sm); Lane #2: Anti-nuclear ribonucleoprotein antibodies (nuclear RNP); Lane #3: Anti-ribosomal ribonucleoprotein (ribosomal RNP); Lane #4: Anti-Ro (SS-A)/Anti-La (SS-B) antibodies; Lane#5: Anti-Jo-1 antibodies (Jo-1); Lane#6: Anti-Scl-70 antibodies (Scl-70); Lane #7: Anti-histone antibodies (histones). Prototype sera used in the Western blot were derived from patients with rheumatic diseases and established as secondary standards for the indicated autoantibodies by demonstration of immunological identity with primary standard sera for that specificity, including sera obtained from the U.S. Centers for Disease Control.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. device comprised of a housing surrounding a plurality of channels each of which encloses a separate reaction zone:
    a first reaction zone comprising a porous membrane and a first electrode assembly in fluid communication with a first channel, the first reaction zone comprising a complex target extract that includes a mixture of autoantigens prepared from a crude cellular extract and supplemented with chromatin and other autoantibody-capturing molecules that together present a heterogeneous mixture of total autoantigens immobilized to the porous membrane, and the first electrode assembly in communication with an amperometric reader;
    a second reaction zone comprising a porous membrane and a second electrode assembly in fluid communication with a second channel, the second reaction zone comprising either the same heterogeneous mixture of autoantigens immobilized to the porous membrane or IgG immunoglobulin immobilized to the porous membrane, serving as a positive control, and the second electrode assembly in electrical communication with the amperometric reader;
    and a source of negative pressure in fluid communication with the first reaction zone and the second reaction zone.

2. The device of claim 1 further including a third reaction zone comprising a porous membrane and a third electrode assembly in fluid communication with a third channel, the third reaction zone being a blank membrane devoid of any potential reactant and serving as a negative control the third electrode assembly in communication with the amperometric reader and in fluid communication with the source of negative pressure.

3. A method in which a biological sample from a subject to be tested for autoantibodies is placed in the first and in the third channels of the device described in claim 2 and is drawn through the first and third reaction zones by negative pressure to permit at least a portion of autoantibodies in the biological sample to be captured by one or more components of the heterogeneous mixture of autoantigens immobilized on the membrane in the first channel and failing to be captured by the blank membrane in channel three;
    rinsing unbound or loosely bound components of the biological sample from reaction zones in channels one and three with a detergent-containing solution using negative pressure;
    drawing by negative pressure an anti-human antibody through channels one, two, and three, the anti-human antibody being conjugated to an enzyme that can catalyze an electrode-detectable reaction in the presence of a suitable substrate;
    rinsing away anti-human antibody/enzyme conjugate that had not bound to the reaction zones in the three channels with a detergent-containing solution using negative pressure;
    contacting the suitable substrate of the enzyme with the three reaction zones under conditions appropriate for the conjugated enzyme to catalyze an electrode-detectable reaction; and
    measuring the electrode-detectable reaction with the amperometric reader.

4. The method of claim 3 in which a difference between the measured electrode-detectable reaction in channel one containing the heterogeneous mixture of autoantigens and a measured electrode-detectable reaction in channel three containing the blank membrane provides a quantitative value for the total autoantibody activity in the biological sample derived from the subject.

5. The method of claim 3 performed in no more than 30 minutes and while the subject is present at a point-of-care clinic.

* * * * *